United States Patent
Ito et al.

(10) Patent No.: US 6,616,920 B1
(45) Date of Patent: Sep. 9, 2003

(54) NAIL-CARE COMPOSITION CONTAINING NAIL-CARE POLYMER

(75) Inventors: Kayo Ito, Yokkaichi (JP); Tomoaki Hiwatashi, Yokkaichi (JP); Shigeoki Kawaguchi, Yokkaichi (JP); Yukio Saito, Yokkaichi (JP); Kazuhide Hayama, Yokkaichi (JP)

(73) Assignee: Mitsubishi Chemical America, Inc., White Plains, NY (US)

( * ) Notice: Subject to any disclaimer, the term of this patent is extended or adjusted under 35 U.S.C. 154(b) by 0 days.

(21) Appl. No.: 09/643,964

(22) Filed: Aug. 23, 2000

(30) Foreign Application Priority Data

Aug. 23, 1999 (JP) ............................................. 11-235219

(51) Int. Cl.$^7$ ................................................. A61K 7/04
(52) U.S. Cl. ............................................ 424/61; 514/63
(58) Field of Search ................................ 424/61; 514/63

(56) References Cited

U.S. PATENT DOCUMENTS

| 4,303,772 A | * 12/1981 | Novicky ................. 351/160 H |
| 4,358,567 A | 11/1982 | Hayama et al. |
| 4,414,375 A | * 11/1983 | Neefe ........................ 526/260 |
| 5,045,621 A | 9/1991 | Suzuki |
| 5,061,481 A | 10/1991 | Suzuki et al. |
| 5,166,276 A | 11/1992 | Hayama et al. |
| 5,219,560 A | 6/1993 | Suzuki et al. |
| 5,480,634 A | 1/1996 | Hayama et al. |
| 5,832,884 A | 11/1998 | Haas et al. |
| 6,123,933 A | * 9/2000 | Hayama et al. ................ 424/69 |
| 6,375,932 B1 | * 4/2002 | Hiwatashi et al. ............ 424/45 |

FOREIGN PATENT DOCUMENTS

| EP | 0 754 444 | 1/1997 |
| JP | 2-003417 | 1/1990 |
| JP | 5-213719 | 8/1993 |
| JP | 8-143427 | 6/1996 |
| JP | 8-283358 | 10/1996 |
| JP | 9-183711 | 7/1997 |

OTHER PUBLICATIONS

Y. Kawakami, et al., Polymer Journal, vol. 14, No. 11, pps. 913–917, "Silicone Macromers for Graft Polymer Synthesis," 1982.

A.T. Holohan, et al., Macromol. Chem. Phys., vol. 195, pps. 2965–2979, "Monofunctional Polydimethylsiloxane Oligomers for Graft Copolymerisation," 1994.

* cited by examiner

*Primary Examiner*—Jyothsan Venkat
(74) *Attorney, Agent, or Firm*—Oblon, Spivak, McClelland, Maier & Neustadt, P.C.

(57) ABSTRACT

The invention provides a nail-care polymer with great adhesion to nail, good surface smoothness and gloss and high coating durability for use in a nail-care product.

18 Claims, No Drawings

NAIL-CARE COMPOSITION CONTAINING NAIL-CARE POLYMER

BACKGROUND OF THE INVENTION

1. Field of the Invention

The present invention relates to a nail-care composition such as a nail enamel, a nail enamel base coat and a nail enamel top coat, a method of coating nails and a kit for coating nails, in which the nail-care composition comprises a nail-care polymer recovered by copolymerizing a polysiloxane compound of a specific structure with a radical polymerizable monomer.

2. Description of the Related Art

Polymers prepared by copolymerization of monomers with polysiloxane group for use in nail-care products are described in Japanese Patent Laid-open Nos. 5-213719/1994, 8-143427/1996 and 9-183711/1997. In these nail-care polymers, great characteristic properties of polysiloxane are actively utilized. Therefore, these nail-care polymers can give great gloss and smooth touch to nail, owing to the great drying properties.

However, these polymers are all copolymers of silicone macromonomer with a radical polymerizable unsaturated bond on one end with other monomers, so the reactivity of silicone macromonomer is insufficient although the smoothness can be improved. Particularly when high-molecular silicone macromonomer is used, the macromonomer unreactive is likely to remain. When such unreactive macromonomer remains, the macromonomer exerts its action as a plasticizer of the coating film after drying, so that the film strength is decreased or the adhesion is decreased due to bleed out, which can disadvantageously cause peeling off or insufficient adhesion between coatings when used in lamination, leading to insufficient durability. As described above, no nail-care polymer with entirely satisfactory performance has been heretofore produced.

Hair-care products containing a copolymer containing a hydrophilic unsaturated monomer and an unsaturated monomer having a polysiloxane group, in which the polysiloxane group-containing monomer has at least one unsaturated group are disclosed in U.S. Pat. Nos. 5,166,276 and 5,480,634.

SUMMARY OF THE INVENTION

It is a purpose of the invention to provide a nail-care composition comprising a nail care polymer with great adhesion to nail, good surface smoothness and gloss and high coating durability when used in a nail-care product. Additionally, it is the other purpose of the invention to provide a nail-care composition comprising a nail-care polymer with excellent adhesion between layers when used as base coat and top coat.

It is another embodiment of the present invention to provide a method of coating nails with a nail-care composition.

It is another embodiment of the present invention to provide a kit comprising a nail-care composition and a brush for applying said nail care composition.

So as to attain the purposes, the present inventors have made various investigations. The inventors have found that a polymer with satisfactorily great performance for use in nail-care products can be produced by using a specific quantity of a specific polysiloxane compound with radical polymerizable unsaturated bonds at both the ends. Thus, the invention has been achieved.

In accordance with the invention, more specifically, it is provided a nail-care composition comprising a nail-care polymer of a weight average molecular weight of 30,000 to 1,500,000, comprising 0.5 to 90% by weight of a constitutive unit derived from a polysiloxane compound with radical polymerizable unsaturated bonds on both the ends of the molecular chain as represented by the following formula (1) (sometimes abbreviated as "Compound A" hereinbelow) and 10 to 99.5% by weight of a constitutive unit derived from a radical polymerizable monomer copolymerizable with the Compound A (sometimes abbreviated as "Compound B" hereinbelow):

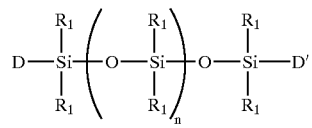

where D and D' may be the same or different and each independently represent an unsaturated bond-containing group represented by the following formula (2) or (3):

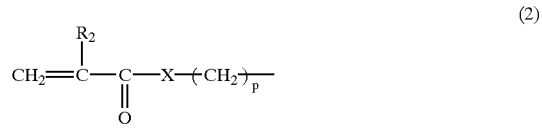

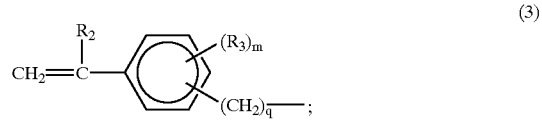

$R_1$ and $R_3$ may be the same or different and represent hydrogen atom, an alkyl group with one to 10 carbon atoms, aryl group, or a polyoxyalkylene group with the end substituted with hydroxyl group, alkoxyl group or alkylcarbonyloxy group; $R_2$ represents hydrogen atom or methyl group; X represents amino (—NH—) group or oxygen atom; n represents an integer of 4 to 500; p represents an integer of 1 to 4; q represents an integer of 0 to 4; and m represents an integer of 0 to 4.

In one preferable embodiment of the invention, it is provided the nail-care polymer wherein n is an integer of 50 to 500 in the compound of the formula (1) the nail-care polymer wherein the ratio of the content of the constitutive unit derived from the Compound A is within a range of 0.5 to 50% by weight; the nail-care polymer wherein the ratio of the content of the constitutive unit derived from the Compound B is within a range of 50 to 99.5% by weight; or the nail-care polymer wherein the constitutive unit derived from the Compound B comprises a constitutive unit derived from a hydrophilic unsaturated monomer (sometimes abbreviated as Compound B1 hereinbelow) or a mixture comprising the aforementioned constitutive unit and a constitutive unit derived from a hydrophobic unsaturated monomer (sometimes abbreviated as Compound B2 hereinbelow) and the ratio in weight of the contents of the Compound B1 and the Compound B2 (sometimes abbreviated as B1/B2 hereinbelow) is within a range of preferably 0/100 to 75/25, more preferably 0/100 to 40/60.

In another preferable embodiment of the invention, it is provided the nail-care polymer wherein the Compound B1 is a monomer selected from the group consisting of a hydrophilic unsaturated monomer with a nonionic group, an anionic group, a cationic group or an amphoteric ion group;

the nail-care polymer wherein the Compound B1 is a monomer selected from the group consisting of a hydrophilic unsaturated monomer with a cationic group (sometimes abbreviated as cationic monomer hereinbelow), a mixture of the cationic monomer and a hydrophilic unsaturated monomer with an anionic group, a hydrophilic unsaturated monomer with an amphoteric ion group (sometimes abbreviated as amphoteric ion monomer hereinbelow), and a mixture of the amphoteric ion monomer and the cationic monomer, or a mixture thereof; the nail-care polymer wherein the Compound B1 is at least one compound selected from the group consisting of acrylic acid, methacrylic acid, an acrylate salt and a methacrylate salt; the nail-care polymer wherein the Compound B1 is an amphoteric compound represented by the following formula (4)

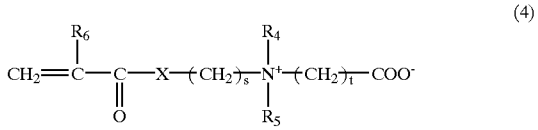

(4)

where
R$_6$ represents hydrogen atom or methyl group; R$_4$ and R$_5$ independently represent an alkyl group with one to 4 carbon atoms; X represents amino (—NH—) group or oxygen atom; s represents an integer of 2 to 6; and t represents an integer of 1 to 4;
or the nail-care polymer wherein the Compound B1 is an amine oxide compound represented by the following formula (5):

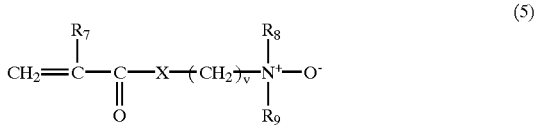

(5)

where
R$_7$ represents hydrogen atom or methyl group; R$_8$ and R$_9$ independently represent an alkyl group with one to 4 carbon atoms; X represents amino (—NH—) group or oxygen atom; and v represents an integer of 2 to 6.

In accordance with another embodiment of the invention, kit comprising a nail-care composition comprising the nail-care polymer and an applicator for said nail-care composition is additionally provided, together with a nail-care method comprising coating the nail-care composition on a nail.

DETAILED DESCRIPTION OF THE PREFERRED EMBODIMENTS

The nail-care polymer of the invention is a polymer of a weight average molecular weight of 30,000 to 1,500,000, comprising 0.5 to 90% by weight of a constitutive unit derived from a polysiloxane compound (Compound A) with radical polymerizable unsaturated bonds at both the ends of the molecular chain as represented by the formula (1), and 10 to 99.5% by weight of a constitutive unit derived from a radical polymerizable monomer (Compound B) copolymerizable with the Compound A.

Additionally, the Compounds A and B individually comprise only one type of each of such compounds or two or more types of each of such compounds in combination, as long as the contents thereof are within the ranges described above.

Compound A: Polysiloxane Compound

The polysiloxane compound as the Compound A is represented by the following formula (1).

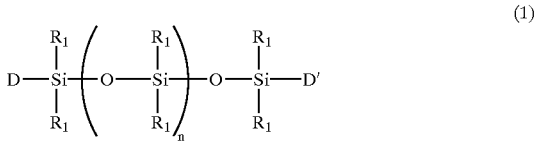

(1)

in the formula, R$_1$ may be the same or different and independently represents hydrogen atom, an alkyl group with one to 10 carbon atoms, aryl group, or a polyoxyalkylene group with the end substituted with hydroxyl group, alkoxyl group or alkylcarbonyloxy group; D and D' may be the same or different and each independently represent unsaturated bond-containing group represented by the following formula (2) or (3); n represents an integer of 4 to 500, preferably an integer of 30 to 500, more preferably an integer of 50 to 400.

(2)

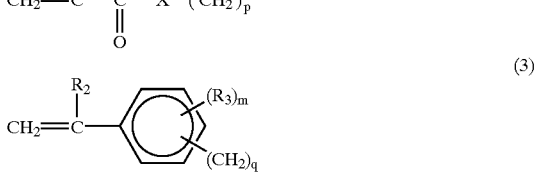

(3)

in the formula, R$_2$ represents hydrogen atom or methyl group; X represents amino (—NH—) group or oxygen atom; R$_3$ may be the same or different and represents hydrogen atom, an alkyl group with one to 10 carbon atoms, aryl group, or a polyoxyalkylene group with the end substituted with hydroxyl group, alkoxyl group or alkylcarbonyloxy group; p represents an integer of 1 to 4; q represents an integer of 0 to 4; and m represents an integer of 0 to 4.

In the definition of the substituents in the formulas (1) and (3), the alkyl group with one to 10 carbon atoms for R$_1$ and R$_3$ includes linear or branched alkyl groups with one to 10 carbon atoms, for example methyl, ethyl, n-propyl, isopropyl, n-butyl, heptyl, 2-ethylhexyl and n-octyl; the aryl group, preferably has six to twenty carbon atoms, more preferably six to ten carbon atoms, includes as exemplary species, phenyl and benzyl; the alkoxyl group means an alkoxyl group with an alkyl moiety with one to 10 carbon atoms; the alkylcarbonyloxy group means an alkylcarbonyloxy group with an alkyl moiety with one to 10 carbon atoms; and these alkyl moieties are preferably with one to 4 carbon atoms; and additionally, the polyoxyalkyl moiety of the substituted polyoxyalkylene group includes for example polyoxyalkylene chain represented by the following formula (8):

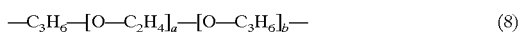

(8)

in the formula, a and b represent an integer of 0 to 5, provided that the sum of a and b is within a range of 1 to 10. In a preferred embodiment a is an integer of from 1 to 5, and b is an integer of from 0 to 3.

The substituted polyoxyalkylene group includes polyoxyalkylene groups with the carbon ends of the polyoxyalkylene chains being substituted with hydroxyl group, the alkoxyl group or the alkylcarbonyloxy group.

Among them, $R_1$ and $R_3$ preferably include hydrogen atom, methyl group, ethyl group, propyl group, n-butyl group and 2-ethylhexyl group; most preferably, $R_1$ is methyl group and $R_3$ is hydrogen atom. Additionally, the binding position of the group —$(CH_2)_q$— in the formula (3) may be o-, m- or p-positions, most preferably the p-position.

When the polymerization degree n of the polysiloxane moiety in the Compound A is below 4, the effect of the silicone compound on the improvement of smoothness is insufficient; above 500, the copolymerizability with other radical polymerizable monomers is reduced, unpreferably. When n is within a range of 50 to 500, more preferably, the smoothness is particularly great.

Because the Compound A has radical polymerizable unsaturated bonds at both the ends of the molecular chain, the probability of the incorporation of the Compound A is high during the copolymerization with other radical polymerizable monomers; thus, the possibility that the Compound A remains as it is unreactive to consequently soften the generated coating film or cause bleed out can be reduced.

When the Compound A with a polymerization degree n as high as 50 to 500 is used, the crosslinking density is not so elevated even if the Compound A has two polymerizable unsaturated bonds, so that gelation possibility can be reduced. Because the Compound A produces thereby an appropriate crosslinking structure, additionally, the molecular weight of the resulting copolymer can be elevated, so that the strength of the coating film after drying can be elevated to give a nail-care product with great durability.

The polysiloxane compound represented by the aforementioned formula (1) is available commercially (manufactured by Chisso, Ltd.), including for example SilaPlane FM 7725 under trade name (in the formula (1), D and D' represent the group of the formula (2); $R_1$ represents methyl group; $R_2$ represents methyl group; X represents oxygen atom; p is 3; and n is 130); SilaPlane FM 7726 under trade name (in the formula (1), D and D' represent the group of the formula (2); $R_1$ represents methyl group; $R_2$ represents methyl group; X represents oxygen atom; p is 3; and n is 270); and SilaPlane FM 7727 under trade name (in the formula (1), D and D' represent the group of the formula (2); $R_1$ represents methyl group; $R_2$ represents methyl group; X represents oxygen atom; p is 3; and n is 410).

The polysiloxane compound of the formula (1) may be produced by conventional methods known to those of ordinary skill in the art, such as according to descriptions, for example, in Polymer J., (Tokyo) 14 (11), 913 (1982), Macromol. Chem. Phys. 195, 2965 (1994), Japanese Patent Publication No. 3417/1990 and U.S. Pat. No. 5,045,621, the relevant contents of which are hereby incorporated by reference.

More specifically, the polysiloxane compound of the formula (1) can be produced, for example, by anion polymerizing a cyclic siloxane represented by the following formula (9):

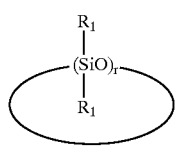

(9)

where, $R_1$ represents the same meaning as described above; and r represents an integer of 3 to 4, using an organosilane alkali metal salt represented by the following formula (2-1) or (3-1) as a polymerization initiator:

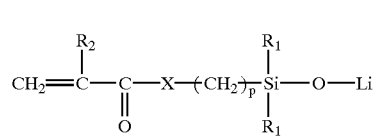

(2-1)

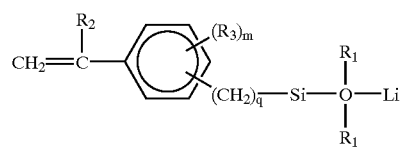

(3-1)

in the formulas, $R_1$, $R_2$, $R_3$, p, q and m represent the same meanings as described above and terminating the polymerization with a silicone compound represented by the following formula (2-2) or (3-2):

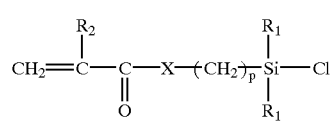

(2-2)

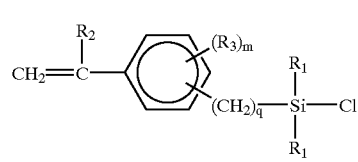

(3-2)

in the formulas, $R_1$, $R_2$, $R_3$, p, q and m represent the same meanings as described above.

Herein, the cyclic siloxane of the formula (9) is a compound known per se and is readily available. Specific examples of the compound of the formula (9) includes for example hexamethylcyclotrisiloxane, ocatamethylcyclotetrasiloxane, hexaethylcyclotrisiloxane, octethylcyclotetrasiloxane, hexaphenylcyclotrisiloxane, and octaphenylcyclotetrasiloxane. Among them, hexamethylcyclotrisiloxane and ocatamethylcyclotetrasiloxane are preferable; hexamethylcyclotrisiloxane is particularly preferable among them.

Compounds of the formulas (2-1), (3-1), (2-2) and (2-3) can be prepared synthetically according to production methods known per se, for example methods described in the aforementioned references.

Compound B: Radical Polymerizable Monomer Copolymerizable with Compound A

The Compound B composing one constitutive unit of the nail-care polymer of the invention is with no specific limitation. Hydrophilic unsaturated monomer (Compound B1) and/or hydrophobic unsaturated monomer (Compound B2) can be used as such, wherein the ratio in weight of the contents of the Compound B1 and the Compound B2 in the polymer is preferably within a range of 0/100 to 75/25, more preferably within a range of 0/100 to 40/60, most preferably 1/99 to 30/70.

Hydrophilic Unsaturated Monomer (Compound B1)

In accordance with the invention, the hydrophilic unsaturated monomer is at a water solubility at 25° C. of 10 g/100 g. water or more, while the hydrophobic unsaturated monomer means unsaturated monomers except for the hydrophilic unsaturated monomer.

The hydrophilic unsaturated monomer (Compound B1) preferably includes the following 4 types. However, the classification is just for convenience. Therefore, monomers corresponding to two or more groups are also present.

1. Monomer with nonionic groups, anionic groups, cationic groups or amphoteric ion groups.
2. Acrylic acid or salts thereof, methacrylic acid or salts thereof.
3. Amphoteric compound represented by the following formula (4) or compounds generating through an amphoterization process the amphoteric compound.

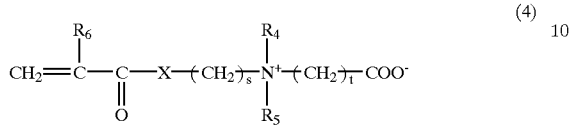

in the formula, $R_6$ represents hydrogen atom or methyl group; $R_4$ and $R_5$ independently represent an alkyl group with one to 4 carbon atoms; X represents amino (—NH—) group or oxygen atom; s represents an integer of 2 to 6; and t represents an integer of 1 to 4.

As described above, the monomer B1, which gives rise to an amphoteric group in the polymer may be a monomer which lacks an amphoteric group, however, after polymerization may be easily converted to an amphoteric group. Suitable amphoteric group precursors, polymerization processes conversion methods of the amphoteric group precursor to an amphoteric group (amphoterization process) are described for example, in U.S. Pat. No. 4,358,567 and Japanese laid-open No. 8-283358/1996, the relevant portions of which are hereby incorporated by reference.

4. Amine oxide compound represented by the following formula (5) or compounds generating through a N-oxidation process of the corresponding amine

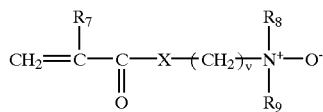

where $R_7$ represents hydrogen atom or methyl group; $R_8$ and $R_9$ independently represent an alkyl group with one to 4 carbon atoms; X represents amino (—NH—) group or oxygen atom; and r represents an integer of 2 to 6. Suitable examples of the amine oxide compoud of the formula (5) and the corresponding amine are described in EP 0754,444, the relevant portions of which are hereby incorporated by reference. Polymerization of the corresponding amine and subsequent oxidation to the corresponding amine oxide (N-oxidation process) may be done by conventional methods known to those of ordinary skill in the art without undue experimentation, such as that described in EP 0754,444. Within the context of the present invention, the corresponding amine of an N-oxide would be clear to those of ordinary skill the art, for example would be an amine resulting from reduction of the oxygen of an N-oxide.

In the specification, herein, the alkyl group with one to 4 carbon atoms includes linear or branched alkyl groups with one to 4 carbon atoms, such as methyl, ethyl, n-propyl, iso-propyl, n-butyl, sec-butyl, and tert-butyl.

The following monomers are illustrated as the monomers a to d described above in 1:
a. monomer with cationic group;
b. monomer with anionic group;
c. monomer with nonionic group; and
d. monomer with amphoteric ion group.

a. Monomer with Cationic Group (Cationic Monomer)
a-1. (Meth)acrylate hydroxypropyltrimethylammonium chloride, (meth)acrylate hydroxypropyltriethylammonium bromide, etc., as monomers derived from acrylic acid or methacrylic acid collectively referred to as "(meth)acrylic acid" hereinbelow; acrylate and methacrylate are collectively referred to as "(meth)acrylate" hereinbelow and quaternary epichlorohydrins with one to 4 carbon atoms.
a-2. Dimethylaminoethyl(meth)acrylate, diethylamino (meth)acrylate and dimethylaminopropyl(meth) acrylate as amine derivatives derived from acrylamide or methacrylamide, collectively referred to as "(meth) acrylamide", or (meth)acrylic acid and dialkylalkanolamine with an alkyl group with one to 4 carbon atoms, or dimethylaminopropyl(meth)acrylamide.
a-3. Neutralized products of the compound described above in 2 with acids such as hydrochloric acid and lactic acid; modified products of the compound described above in 2 with halogenated alkyls such as methyl chloride, ethyl chloride, methyl bromide, and ethyl iodide; modified products of the compound described above in 2 with halogenated fatty acid esters such as ethyl chloroacetate and methyl chloropropionate; and modified products of the compound described above in 2 with dialkylsulfuric acids such as dimethylsulfuric acid and diethylsulfuric acid.
a-4. Amine derivatives of allyl compounds such as diallyldimethylammonium chloride.

These cationic monomers can be used in such forms of monomers for polymerization. Precursors thereof capable of generating such cationic groups through modification with so-called modification agents after polymerization can satisfactorily be used. For example, a method is just illustrated therefor, comprising a copolymerization process using dimethylaminoethyl(meth)acrylate and a subsequent cationic preparation process using hydrochloric acid, monochloroacetate ethyl and dimethylsulfuric acid described above.

b. Monomer with Anionic Group (Sometimes Abbreviated as Anionic Monomer Hereinbelow)
b-1. α,β-unsaturated carboxylic acids such as (meth) acrylic acid, maleic acid, maleic anhydride, itaconic acid, fumaric acid and crotonic acid;
b-2. Semi-esters of unsaturated polybasic acid anhydrides (for example, succinic anhydride and phthalic anhydride) and hydroxyl group-containing (meth) acrylates such as hydroxyethyl(meth)acrylate and hydroxypropyl(meth)acrylate.
b-3. Monomers with sulfonate group, such as styrenesulfonic acid and sulfoethyl(meth)acrylate.
b-4. Phosphate group-containing monomers, such as acid phosphooxyethyl(meth)acrylate, and 3-chloro-2-acid phosphooxypropyl(meth)acrylate.

These anionic monomers can be used as they are in acid form or after partial neutralization or complete neutralization, or after partial or complete neutralization after copolymerization thereof at their acid state.

The basic compound for use in neutralization is with no specific limitation as long as neutralization is possible with the basic compound. For example, the basic compound includes alkali metal hydroxides such as lithium hydroxide, potassium hydroxide and sodium hydroxide; amine compounds such as aqueous ammonia, mono-, di- or triethanolamine, triethylamine, morpholine, aminomethylpropanol, and aminoethylpropanediol.

c. Monomer with Nonionic Group (Sometimes Abbreviated as Nonionic Monomer Hereinbelow)

Monomers derived from (meth)acrylic acid and (meth) acrylamide along with alkylene oxides with 2 to 4 carbon atoms, such as hydroxyethyl(meth)acrylate, polyethylene glycol mono(meth)acrylate, methoxypolyethylene glycol mono(meth)acrylate, methoxypoly(ethylene glycol/propylene glycol)mono(meth)acrylate and (meth) acrylamide; and acrylamide and N-vinylpyrrolidone.

d. Monomer with Amphoteric Ion Group (Amphoteric Ion Monomer)

Modified products of the amine derivatives of the (meth) acrylic acid and the (meth)acrylamide derivatives, for example dimethylaminoethyl(meth)acrylate and dimethylaminopropyl(meth)acrylamide, with halogenated fatty acid salts including for example monochloroacetate aminomethylpropanol salt, monochloroacetate triethanolamine salt, potassium monochloroacetate and sodium monobromopropionate, and modified products thereof with propane sultone and with oxides.

Like the cationic monomers, these amphoteric ion monomers can satisfactorily be used in the form of monomers for polymerization; as another method, these amphoteric ion monomers can be copolymerized in the form of precursors and subsequently prepared as amphoteric compounds by using modification agents according to the description in, for example U.S. Pat. No. 4,358,567. In case that salts are generated as byproducts through such amphoteric preparation process, these salts can be removed by filtration and ion exchange, if necessary.

Among the monomers, additionally, preference is given to monomers selected from the cationic monomers, mixtures of the cationic monomers and anionic monomers, the amphoteric ion monomers and mixtures of the amphoteric ion monomers and cationic monomers or mixtures thereof.

In case that the mixtures of the cationic monomers and anionic monomers or the amphoteric ion monomers are used, the mixing ratio thereof is preferably 9/1 to 1/9.

As these hydrophilic unsaturated monomers (Compound B1), particularly preferable are as follows.

Acrylic acid or salts thereof, or methacrylic acid or salts thereof, as described in 1-b and 2, an amphoteric compound represented by the formula (9) or compounds generated through an amphoterization process as described in 3, and amine oxide compounds represented by the formula (5) or compounds generated through an N-oxidation process of the corresponding amine as described in 4.

Hydrophobic Unsaturated Monomer (Compound B2)

Hydrophobic unsaturated monomer (Compound B2) is used for the purpose of imparting hydrophobicity to the resulting nail-care polymer and imparting strength, hardness and softness to the film after coating.

Such hydrophobic unsaturated monomer includes for example those described below. However, the classification is just for convenience. Therefore, monomers corresponding to two or more groups may also be present.

e. Saturated or unsaturated (meth)acrylate ester with one to 24 carbon atoms, such as methyl(meth)acrylate, allyl(meth) acrylate, isobutyl(meth)acrylate, t-butyl(meth)acrylate, cyclohexyl(meth)acrylate, octyl(meth)acrylate, 2-ethylhexyl (meth)acrylate, lauryl(meth)acrylate, oleyl(meth)acrylate and behenyl(meth)acrylate.

f. Hydrophobic (meth)acrylate derivatives such as butoxyethyl(meth)acrylate, benzyl(meth)acrylate, tetrahydrofurfuryl(meth)acrylate, ethylene glycol di(meth) acrylate, 1,3-butyleneglycol di(meth)acrylate, and diacetone acrylamide.

g. Aromatic unsaturated monomers such as styrene, chlorostyrene, and vinyltoluene and vinyl esters such as vinyl acetate and vinyl propionate.

Preferable compounds among them are alkyl(meth) acrylates with alkyl groups with one to 18 carbon atoms; preferably, alkyl(meth)acrylates with alkyl groups with one to 4 carbon atoms are effective so as to improve the performance of the film.

The ratio of the hydrophilic unsaturated monomer (Compound B1) and hydrophobic unsaturated monomer (Compound B2) in the Compound B is with no specific limitation as described above; and either one of the Compounds can satisfactorily occupy the entirety. The ratio is generally within a B1/B2 range of preferably 0/100 to 75/25, more preferably 0/100 to 40/60, particularly preferably 1/99 to 30/70.

A polymer at a high content ratio of the Compound B1 is excellent in terms of nail adhesion and film softness, but is poor in terms of moisture resistance, leading to the tendency of low durability. Alternatively, a polymer at a high content ratio of the Compound B2 can generate a hard film with good durability.

When the content ratio of the Compound B2 is more than 75/25 as B1/B2, particularly 40/60, the film strength and water resistance are elevated, preferably, with the resultant improvement of the durability as a nail-care product. The ratio of them (B1/B2) is selected from the respect of the use and characteristic properties of a nail-care product and the gloss and touch after coating.

In case that polyfunctional unsaturated monomers such as ethylene glycol di(meth)acrylate are used as the Compound B2, the polyfunctional unsaturated monomers are preferably used at an amount below 2% by weight of the total monomer weight. Above 2% by weight, the molecular weight of the resulting polymer is so large that gelation may be likely to be induced.

In terms of the molecular weight of bifunctional polysiloxane compound as the Compound A and the amount thereof used, such polyfunctional unsaturated monomers are necessarily used at an amount within a range with no occurrence of gelation of the resulting polymer.

When the alkyl(meth)acrylate with one to 4 carbon atoms is contained at 60% or more in the Compound B2, the hardness is improved so damage does not readily occur, preferably.

The radical polymerizable monomer (Compound B) copolymerizable with the Compound A known per se is generally used and readily available.

Method for Producing Polymer and Physico-chemical Properties of the Resulting Polymer The copolymerization of the Compounds A and B so as to produce the nail-care polymer of the invention can be effected by radical polymerization including mass polymerization, solution polymerization, suspension polymerization and emulsion polymerization.

Among them, solution polymerization comprising dissolving the individual monomers in the solvent, adding a polymerization initiator and agitating the mixture under heating in nitrogen stream is preferable.

The solvent to be used herein includes water; alcohols such as methanol, ethanol, isopropanol, ethylene glycol, butyl cellosolve; ketones such as acetone, methyl ethyl ketone, methylisobutyl ketone; acetate esters such as ethyl acetate and butyl acetate; toluene, xylene, isoparaffin, and cyclic dimethylsiloxane. These solvents are used singly or in combination of two or more thereof.

As the polymerization initiator for example, peroxides such as benzoyl peroxide and lauroyl peroxide; azo compounds such as 2,2'-azobisisobutyronitrile, 2,2'-azobis(2,4-dimethylvaleronitrile), and 2,2'-azobis(4-methoxy-2,4-dimethylvaleronitrile) can be used.

All the types and total amounts of the monomers for use in polymerization can be present satisfactorily from the start of polymerization, but the types and total amounts of the monomers can also be divided and then added in the course of the polymerization. The solvent is preferably used at a volume to a final copolymer concentration of 10 to 65% by weight, more preferably 25 to 50% by weight in the generated copolymer solution.

In the polymer of the invention, the content of the constitutive unit derived from the Compound A is 0.5 to 90% by weight, preferably 0.5 to 50% by weight; the content of the constitutive unit derived from the Compound B is 10 to 99.5% by weight, preferably 50 to 99.5% by weight.

When the content of the constitutive unit derived from the Compound A is below 0.5 % by weight, the property to impart gloss and smooth touch to nail can never be yielded; above 90% by weight, the hardness of the resulting coating film is deteriorated, with the resulting ready damage on nail or insufficient durability.

The weight average molecular weight of the polymer of the invention is 30,000 to 1,500,000, more preferably 50,000 to 1,000,000.

When the molecular weight is below 30,000, the strength of the resulting coating film is insufficient while the moisture resistance is reduced. When the molecular weight is above 1,500,000, the viscosity is elevated, involving difficulty in applying on nail as well as slow drying, which are problematic for use.

The molecular weight of the copolymer can be set at an appropriate value, by appropriately selecting polymerization conditions such as polymerization temperature, the type and amount of a polymerization initiator, the amounts of a solvent and a chain transfer agent to be used.

After removing the solvent from the copolymer solution, the nail-care copolymer can be recovered as solid. Additionally, the solid can be diluted with a solvent and then used as a copolymer solution, satisfactorily. Two or more types of the polymer of the invention and the solution thereof can be mixed together and then used, satisfactorily.

Nail-care Composition

The nail-care composition with great performance can be prepared by using the polymer of the invention in a blend without nitrocellulose or a formula with nitrocellulose.

The amount of the polymer blended in the nail-care composition is with no specific limitation but is generally at 5 to 45% by weight, preferably 10 to 30% by weight, more preferably 15 to 30% by weight. Within the range, a coating film with easy coatability and of an appropriate thickness can readily be prepared.

When blended with nitrocellulose, the amount of nitrocellulose is generally from about 0.1 to 20% by weight, preferably from 2 to 15% by weight.

The solvent for use in the dilution of the polymer includes for example low-molecular esters such as ethyl acetate, propyl acetate, n-butyl acetate, amyl acetate, isobutyl acetate, diacetone alcohol; lower alcohols such as ethanol, isopropanol, n-butanol, n-propanol and t-butanol; ketones such as acetone, methyl ethyl ketone, methyl isobutyl ketone, and cyclohexanone; chlorinated hydrocarbons such as chloroform and dichloromethane; ethers such as diethyl ether, tetrahydrofuran, 1,4-dioxane, cellosolve and carbitol; and hydrocarbons such as toluene, xylene, benzene, hexane, octane and isoper G or H. Among them, preference is given to ethyl acetate, butyl acetate, isopropanol, ethanol, acetone and toluene. These solvents are used singly or in mixture of two or more thereof.

Additionally, a coating solution containing the polymer of the invention can be used in lamination as top coat and base coat, by overlaying the coating solution on nail enamel blended with nitrocellulose or using the coating solution as base coating and overlaying nail enamel containing nitrocellulose thereon.

A nail-care composition with great adhesion between nail and coating film and with great adhesion between coating films, along with great surface smoothness and high durability, can be recovered by using the polymer of the invention according to any of the methods for use.

A nail-care composition with a greater safety profile with no yellowish modification of nail or no pressure on nail can be recovered when the polymer of the invention is used in a formulation with no content of nitrocellulose.

When used in combination with nitrocellulose, the polymer of the invention is greatly miscible with nitrocellulose, so the resulting coating film is transparent and smooth with great dryness and high smoothness, good adhesion to nail, appropriate flexibility and great gloss, along with the characteristic properties of nitrocellulose.

With the nail-care composition of the invention can be blended resins, plasticizers, powders (pigments, dyes, pearl, and the like), organic modified bentonite, solvents, aqueous components, oily components, ultraviolet absorption agents and fragrance for general use in cosmetics, if necessary, in addition to the essential components thereof, with no departure from the scope of the invention. The nail-care polymer of the invention can be used in nail-care compositions such as nail enamel, nail top coat and enamel base coat. Within the context of the present invention formulation of a nail-care composition to achieve the necessary properties suitable for application of the composition to the surface of a nail, is within the level of skill of those of ordinary skill in the art, without undue experimentation. For example determination of suitable viscosity, and solvents to provide for good film forming properties and acceptable drying properties may be achieved by ordinary experimentation. In addition, it is desirable for a nail-care composition to produce a nail coating which is water-proof/water-resistant as well as moisture proof. It is also desirable for the nail coating to be removable by organic solvents such as acetone, ethyl acetate, methyl ethyl ketone and mixtures thereof. In general, esters may be used as solvents and removers. A nail coating composition is also preferably formulated to provide for rapid curing of the coated nail. The formulation of such a nail-composition, to possess such properties, is within the level of skill known to those of ordinary skill in the nail-care art, and may be adjusted based on the specific polymers in the composition, the solvent, concentration and through the use of additives.

The present invention also provides for a method of coating nail by applying to the surface of a nail, the nail-care composition as described above. The method is not particulary limited in terms of the method of applying, however, may typically be applied using an applicator such as a brush.

The present invention also provides for a kit for nail-care comprising a nail-care composition and an applicator for said nail-care composition. The nail-care composition for the kit is as described above. An applicator for a nail-care composition would be readily apparent to those of ordinary skill in the art in the field of nail-care, and can take the form of to a brush of suitable size, bristle composition and stiffness of bristle to allow for application of the nail-care composition to a nail surface.

EXAMPLES

The invention will now be described in the following examples and comparative examples, but the invention is not construed to be limiting to the following examples.

The "part and %" in the following examples represent "part by weight and % by weight", unless otherwise stated. Polysiloxane Compound Used Compound A-1 (for the Examples)

Compound of the following formula (6), with n=130 manufactured by Chisso, Ltd.; SilaPlane FM7725 under trade name

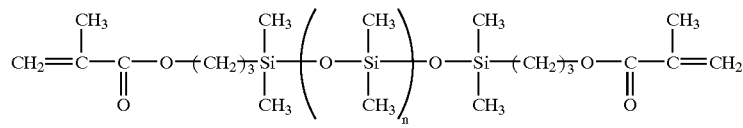

(6)

Compound A-2 (for the Examples)

Compound of the following formula (6), with n=270 manufactured by Chisso, Ltd.; SilaPlane FM7726 under trade name.

Compound A-3 (for the Examples)

Compound of the following formula (6), with n=410 manufactured by Chisso, Ltd.; SilaPlane FM7727 under trade name.

Compound A-4 (for the Comparative Examples)

Polysiloxane compound with a double bond at one end and of the following formula (7) manufactured by Chisso, Ltd.; SilaPlane FM0725 under trade name.

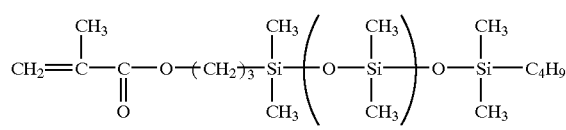

(7)

Evaluation Method

1. Evaluation of adhesion to nylon plate

Nail enamel was applied on a nylon board by using an applicator of a clearance of 100 μm; after drying for 24 hours, the adhesion was evaluated by using cross cut test (100 section of 1 mm×1 mm) on the following standard.

| Score | Evaluation standard |
|---|---|
| 4 | smooth cut with no peeling |
| 3 | slight peeling at cross points of cuts |
| 2 | slight peeling of section due to cut |
| 1 | most or all sections peeled off |

2. Evaluation by panelists

Nail enamel was applied on the nails on both the hands of 10 volunteers; one day later, the utility such as durability, smoothness and surface damage of nail enamel was evaluated on the following 4-grade standard by the individual panels. The mean was calculated.

2-1. Durability

Nail enamel was coated on nail; one day later, the state of the coating film was visually evaluated.

| Score | Evaluation standard |
|---|---|
| 4 | no peeling on top end; almost no scrape |
| 3 | no peeling on top end, prominent scraping |
| 2 | slight peeling at top end |
| 1 | severe peeling |

2-2. Smoothness

Smoothness of the surface of the coating film one day after coating on nail was evaluated.

| Score | Evaluation standard |
|---|---|
| 4 | very smooth |
| 3 | Moderately smooth |
| 2 | not so smooth |
| 1 | not smooth but hooking touch |

2-3. Surface gloss retention

The state of the surface one day after coating on nail was visually evaluated.

| Score | Evaluation standard |
|---|---|
| 4 | almost no damage; good gloss |
| 3 | slight damage |
| 2 | damage with poor gloss |
| 1 | more damage with no gloss |

Production of Polymer

Production Example 1

Into a five-neck flask equipped with a ref lux condenser, a dropping funnel, a thermometer, a glass tube for nitrogen substitution and an agitation apparatus were charged 300 parts of butyl acetate. Under agitation, the temperature of the system was raised to 80° C. in nitrogen stream, to which was added 0.4 part of dimethyl 2,2'-azobisisobutyrate. Then, a mixture of 5 parts of acrylic acid, 35 parts of tert-butyl methacrylate, 50 parts of butyl methacrylate, and 10 parts of the polysiloxane compound as Compound A-1 was added to the reaction system from the dropping funnel over one hour; continuously, the temperature was retained at 80° C. in nitrogen stream, for 2-hr polymerization. Further, 0.5 part of 2,2'-azobisisobutyrate dimethyl was added, for 5-hr polymerization, to recover Polymer P-1.

The weight average molecular weight of the Polymer P-1 (on a polystyrene basis) was measured by GPC (gel permeation chromatography), which was 140,000.

Production Example 2

In the same manner as in Production Example 1, except for the substitution of the Compound A-1 with Compound A-4, Polymer P-2 was recovered. The weight average molecular weight of Polymer P-2 as determined in the same manner as in Production Example 1 was 58,000.

Production Example 3

In a five-neck flask identical to that in Production Example 1 were charged 150 parts of acetone, which was then heated to the boiling point in nitrogen stream, followed by addition of 0.2 part of 2,2'-azobis(2,4-dimethylvaleronitrile). Subsequently, 80 parts of methyl methacrylate, 18 parts of lauryl methacrylate and 2 parts of Compound A-1 were dropwise added through a dropping funnel into the reaction mixture over one hour; subsequently, the resulting mixture was heated at the boiling point under reflux in nitrogen stream, for polymerization for 2 hours. Furthermore, 0.5 part of 2,2'-azobis(2,4-dimethylvaleronitrile) was added twice every 3 hours for polymerization, to recover Polymer P-3. The weight average molecular weight of the Polymer P-3 was 86,000.

Production Example 4

In a five-neck flask identical to that in Production Example 1 were charged 100 parts of ethyl acetate, 0.6 part of 2,2'-azobisisobutyronitrile, 10 parts of dimethylaminoethyl methacrylate, 35 parts of methyl methacrylate, 50 parts of butyl methacrylate and 5 parts of Compound A-2, and the resulting mixture was heated at the boiling point under ref lux in nitrogen stream, for polymerization for 8 hours.

After completion of the polymerization, aqueous 34% hydrogen peroxide of an equimolar number to that of dimethylaminoethyl methacrylate was dropwise added through a dropping funnel into the reaction mixture and was then heated under reflux at the boiling point in nitrogen stream, for a reaction for oxide preparation for 12 hours. The weight average molecular weight of the resulting Polymer P-4 was 82,000.

Production Example 5

A polymer solution was prepared by the same method as in Production Example 4. After completion of the polymerization, an anhydrous 40% ethanol suspension of potassium hydroxide-neutralized monochloroacetic acid of an equimolar number to that of dimethylaminoethyl methacrylate was dropwise added in place of aqueous hydrogen peroxide through a dropping funnel into the reaction mixture followed by heating under reflux at the boiling point in nitrogen stream, for another 12 hours for amphoteric reaction. From the resulting viscous suspension was filtered the suspended material with a filtration apparatus under pressure, to recover Polymer P-5.

Production Example 6

In a five-neck flask identical to that in Production Example 1 were charged 200 parts of anhydrous ethanol, 0.2 part of 2,2'-azobisisobutyronitrile, 3 parts of dimethyiaminoethyl methacrylate, 50 parts of methyl methacrylate, 37 parts of 2-ethylhexyl methacrylate and 10 parts of Compound, A-2, and the resulting mixture was heated at the boiling point under reflux in nitrogen stream, for polymerization for 9 hours. Every 3 hours during polymerization, 0.4 part of 2,2'-azobisisobutyronitrile was added.

After completion of the polymerization, diethyl sulfuric acid of an equimolar number to that of dimethylaminoethyl methacrylate was dropwise added through a dropping funnel into the reaction mixture and was then heated under reflux at 60° C. in nitrogen stream, for a cationic reaction for 5 hours. The weight average molecular weight of the resulting Polymer P-6 was 120,000.

Production Example 7

In a five-neck flask identical to that in Production Example 1 were charged 200 parts of butyl acetate, 0.25 part of 2,2'-azobisisobutyronitrile, 5 parts of acrylic acid, 37 parts of tert-butyl methacrylate, 53 parts of butyl methacrylate, and 5 parts of Compound A-2, and the resulting mixture was heated at 65° C. under reflux in nitrogen stream for 3 hours. Every 3 hours, then, 0.2 part of 2,2'azobisisobutyronitrile was added twice, followed by additional heating under reflux for polymerization. The weight average molecular weight of the resulting Polymer P-7 was 270,000.

Production Example 8

In a five-neck flask identical to that in Production Example 1 were charged 200 parts of ethyl acetate, and the system was heated at the boiling point in nitrogen stream, followed by addition of 0.4 part of 2,2'-azobisisobutyronitrile. Then, 5 parts of acrylic acid, 35 parts of tert-butyl methacrylate, 40 parts of butyl methacrylate and 20 parts of Compound A-3 were added through a dropping funnel into the reaction mixture over one hour, followed by heating under reflux at the boiling point in nitrogen stream, for polymerization for 3 hours. Furthermore, 0.5 part of 2,2'-azobisisobutyronitrile was added for polymerization for 5 hours, to recover Polymer P-8. The weight average molecular weight of the resulting Polymer P-8 was 160,000.

Examples 1 to 8 and Comparative Example 1

The Polymers recovered in Production Examples 1 to 8 were individually blended according to the composition ratios in Table 1, to prepare nail enamels; according to the evaluation methods, nail adhesion, durability, smoothness and surface gloss retention were evaluated on the standards described above. The results are shown in Table 2.

TABLE 1

Nail enamel compositions

|  | Examples 1, 6; Comparative Example 1 | Examples 2 to 5, 7 |
| --- | --- | --- |
| Polymer (solution) | 60% | 50% |
| Ethyl acetate | 33% | 0% |
| Butyl acetate | 0% | 43% |
| Isopropanol | 7% | 7% |

Evaluation Results

As shown in Table 2, consequently, the nail enamels based on the polymers of the invention were all excellent at the utility evaluation by the panelists. The nail enamel of Comparative Example 1 (P-2) was poor in terms of sustainability (durability, surface gloss retention) in particular. It was indicated that the results of the evaluation of the adhesion to nylon plate were not necessarily in correlation with the results of the evaluation of the utility on the nails of the panelists, as shown in Example 2.

TABLE 2

|  | Example 1 | Example 2 | Example 3 | Example 4 | Example 5 | Example 6 | Example 7 | Comparative Example 1 |
|---|---|---|---|---|---|---|---|---|
| Polymers | | | | | | | | |
| types | P-1 | P-3 | P-4 | P-5 | P-6 | P-7 | P-8 | P-2 |
| Weight average molecular weight | 140,000 | 86,000 | 82,000 | 82,000 | 120,000 | 270,000 | 160,000 | 58,000 |
| Composition: compound A (wt. %) | A-1:10 | A-1:2 | A-2:5 | A-2:5 | A-2:10 | A-2:5 | A-3:20 | A-4:10 |
| Composition: compound B-1 (wt. %) | AA:5 | 0 | DMAEMA:10 | DMAEMA:10 | DMAEMA:3 | AA:5 | AA:5 | AA:5 |
| Composition: compound B-2 (wt. %) | tBMA:35 BMA:50 | MMA:80 LMA:18 | MMA:35 BMA:50 | MMA:35 BMA:50 | MMA:50 2EHMA:37 | tBMA:37 BMA:53 | tBMA:35 BMA:40 | tBMA:35 BMA:50 |
| Compound B-1 type | anion | — | oxide through oxidation | amphoteric ion through amphoterization | Cationic Ion through cationization | anion | anion | anion |
| Evaluation (Score) | | | | | | | | |
| adhesion | 3 | 1 | 4 | 3 | 4 | 4 | 4 | 1 |
| durability | 2.8 | 2.6 | 2.9 | 3.0 | 3.2 | 3.7 | 3.9 | 2.3 |
| smoothness | 2.6 | 3.8 | 3.0 | 3.3 | 3.4 | 3.1 | 3.5 | 2.5 |
| surface gloss retention | 3.0 | 3.7 | 3.5 | 3.3 | 3.7 | 3.2 | 3.2 | 2.5 |

AA:acrylic acid
LMA:lauryl methacrylate
DMAEMA:dimethylaminoethyl methacrylate
2EHMA:2-ethylhexyl methacrylate
TBMA:tert-butyl methacrylate
BMA:n-butyl methacrylate
MMA:methyl methacrylate Obviously, numerous modifications and variations of the present invention are possible in light of the above teachings. It is therefore to be understood that within the scope of the appended claims, the invention may be practiced otherwise than as specifically described herein.

This application is based on Japanese patent application JP11-235219 filed in the Japanese Patent Office on Aug. 23, 1999, the entire contents of which are hereby incorporated by reference.

What is claimed is:

1. A nail-care composition comprising a nail-care polymer of a weight average molecular weight of 30,000 to 1,500,000, comprising 0.5 to 90% by weight of a unit derived from polysiloxane compound A represented by the following formula (1):

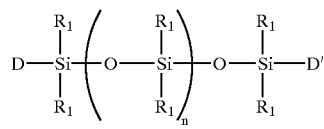

(1)

wherein

D and D' each independently represent an unsaturated bond-containing group represented by the following formula (2) or (3):

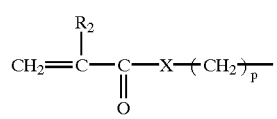

(2)

-continued

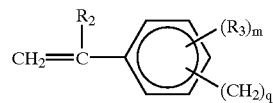

(3)

$R_1$ and $R_3$ may be the same or different and represent hydrogen atom, an alkyl group with one to 10 carbon atoms, aryl group, or a polyoxyalkylene group with the end substituted with hydroxyl group, alkoxyl group or alkylcarbonyloxy group; $R_2$ represents hydrogen atom or methyl group; X represents amino group or oxygen atom; n represents an integer of 4 to 500; p represents an integer of 1 to 4; q represents an integer of 0 to 4; and m represents an integer of 0 to 4;

and 10 to 99.5% by weight of a unit derived from radical polymerizable monomer B, which is copolymerizable with the Compound A wherein the radical polymerizable monomer B comprises hydrophobic unsaturated monomer B2 or a mixture comprising hydrophilic unsaturated monomer B1 and hydrophobic unsaturated monomer B2.

2. The nail-care composition according to claim 1, wherein n is an integer of 50 to 500 in the polysiloxane compound A of the formula 1.

3. The nail-care composition according to claim 1, wherein the ratio of the content of the unit derived from the polysiloxane compound A is within a range of 0.5 to 50% by weight and the ratio of the content of the unit derived from the radical polymerizable monomer B is within a range of 50 to 99.5% by weight.

4. The nail-care composition according to claim 1, wherein the ratio in weight of the contents of the hydrophilic unsaturated monomer B1 and the hydrophobic unsaturated monomer B2 is within a range of 0/100 to 75/25.

5. The nail-care composition according to claim 4, wherein the ratio in weight of the contents of the hydrophilic unsaturated monomer B1 and the hydrophobic unsaturated monomer B2 is within a range of 0/100 to 40/60.

6. The nail-care composition according to claim 4, wherein the hydrophilic unsaturated monomer B1 is a hydrophilic unsaturated monomer with a nonionic group, an anionic group, a cationic group or an amphoteric ion group.

7. The nail-care composition according to claim 4, wherein the hydrophilic unsaturated monomer B1 is a monomer selected from the group consisting of a hydrophilic unsaturated monomer with a cationic group, a mixture of a hydrophilic unsaturated monomer with a cationic group and a hydrophilic unsaturated monomer with an anionic group, a hydrophilic unsaturated monomer with an amphoteric ion group, a mixture of a hydrophilic unsaturated monomer with an amphoteric ion group and a hydrophilic unsaturated monomer with a cationic group, and mixtures thereof.

8. The nail-care composition according to claim 4, wherein the hydrophilic unsaturated monomer B1 is at least one compound selected from the group consisting of acrylic acid, methacrylic acid, an acrylate salt and a methacrylate salt.

9. The nail-care composition according to claim 4, wherein the hydrophilic unsaturated monomer B1 is an amphoteric compound represented by the following formula (4):

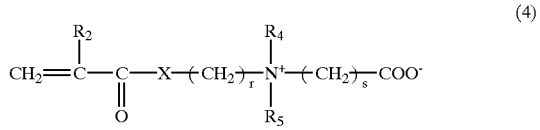

in the formula, $R_2$ represents hydrogen atom or methyl group; $R_4$ and $R_5$ independently represent an alkyl group with one to 4 carbon atoms; X represents amino group or oxygen atom; r represents an integer of 2 to 6; and s represents an integer of 1 to 4 or a compound generating through an amphoterization process the amphoteric compound.

10. The nail-care composition according to claim 4, wherein the hydrophilic unsaturated monomer B1 is an amine oxide compound represented by the following formula (5):

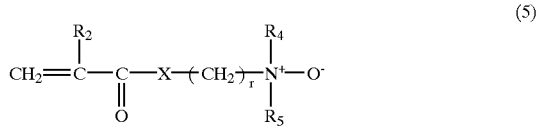

in the formula, $R_2$ represents hydrogen atom or methyl group; $R_4$ and $R_5$ independently represent an alkyl group with one to 4 carbon atoms; X represents amino group or oxygen atom and r represents an integer of 2 to 6 or the corresponding amine.

11. A method of coating nails, comprising applying to a surface of a nail, the nail-care composition of claim 1.

12. A nail-care kit comprising;
  i) the nail-care composition according to claim 1; and
  ii) an applicator for applying said nail-care composition to a surface of a nail.

13. The nail-care composition according to claim 1, wherein the ratio in weight of the contents of the hydrophilic unsaturated monomer B1 and the hydrophobic unsaturated monomer B2 is within a range of 0/100 to 40/60.

14. The nail-care composition according to claim 1, wherein the hydrophilic unsaturated monomer B1 is a hydrophilic unsaturated monomer with a nonionic group, an anionic group, a cationic group or an amphoteric ion group.

15. The nail-care composition according to claim 1, wherein the hydrophilic unsaturated monomer B1 is a monomer selected from the group consisting of a hydrophilic unsaturated monomer with a cationic group, a mixture of a hydrophilic unsaturated monomer with a cationic group and a hydrophilic unsaturated monomer with an anionic group, a hydrophilic unsaturated monomer with an amphoteric ion group, a mixture of a hydrophilic unsaturated monomer with an amphoteric ion group and a hydrophilic unsaturated monomer with a cationic group, and mixtures thereof.

16. The nail-care composition according to claim 1, wherein the hydrophilic unsaturated monomer B1 is at least one compound selected from the group consisting of acrylic acid, methacrylic acid, an acrylate salt and a methacrylate salt.

17. The nail-care composition according to claim 1, wherein the hydrophilic unsaturated monomer B1 is an amphoteric compound represented by the following formula (4):

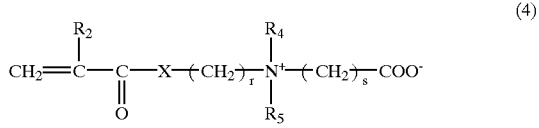

in the formula, $R_2$ represents hydrogen atom or methyl group; $R_4$ and $R_5$ independently represent an alkyl group with one to 4 carbon atoms; X represents amino group or oxygen atom; r represents an integer of 2 to 6; and s represents an integer of 1 to 4 or a compound generating through an amphoterization process the amphoteric compound.

18. The nail-care composition according to claim 1, wherein the hydrophilic unsaturated monomer B1 is an amine oxide compound represented by the following formula (5):

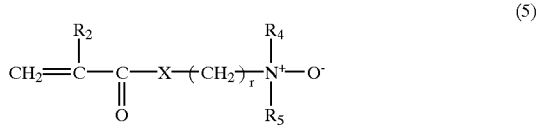

in the formula, $R_2$ represents hydrogen atom or methyl group; $R_4$ and $R_5$ independently represent an alkyl group with one to 4 carbon atoms; X represents amino group or oxygen atom and r represents an integer of 2 to 6 or the corresponding amine.

* * * * *

UNITED STATES PATENT AND TRADEMARK OFFICE
CERTIFICATE OF CORRECTION

| | | |
|---|---|---|
| PATENT NO. | : 6,616,920 B1 | |
| APPLICATION NO. | : 09/643964 | |
| DATED | : September 9, 2003 | |
| INVENTOR(S) | : Ito et al. | |

It is certified that error appears in the above-identified patent and that said Letters Patent is hereby corrected as shown below:

On the title page, the Notice information is incorrect. The Notice information should read:

-- ( * ) Notice: Subject to any disclaimer, the term of this patent is extended or adjusted under 35 U.S.C. 154(b) by 250 days. --

Signed and Sealed this

Fifteenth Day of August, 2006

JON W. DUDAS
*Director of the United States Patent and Trademark Office*